United States Patent
Kim et al.

(10) Patent No.: US 11,957,476 B2
(45) Date of Patent: Apr. 16, 2024

(54) IDENTIFYING A DEMENTIA BASED ON GAZE INFORMATION OF USER PERFORMING TASK ON A SCREEN AND GAZE TASK SCORE

(71) Applicant: Haii co, LTD., Seoul (KR)

(72) Inventors: Ho Yung Kim, Seoul (KR); Bo Hee Kim, Seoul (KR); Dong Han Kim, Seoul (KR); Hye Bin Hwang, Incheon (KR); Chan Yeong Park, Seoul (KR); Ji An Choi, Seoul (KR)

(73) Assignee: HAII CO, LTD., South (KR)

( * ) Notice: Subject to any disclaimer, the term of this patent is extended or adjusted under 35 U.S.C. 154(b) by 0 days.

(21) Appl. No.: 18/058,603

(22) Filed: Nov. 23, 2022

(65) Prior Publication Data
US 2023/0233137 A1     Jul. 27, 2023

(30) Foreign Application Priority Data
Jan. 21, 2022   (KR) .................. 10-2022-0008986

(51) Int. Cl.
| | |
|---|---|
| A61B 5/00 | (2006.01) |
| A61B 3/113 | (2006.01) |
| A61B 3/14 | (2006.01) |
| A61B 5/16 | (2006.01) |
| G06T 7/246 | (2017.01) |
| G06V 10/56 | (2022.01) |
| G06V 40/18 | (2022.01) |
| G06V 40/20 | (2022.01) |

(52) U.S. Cl.
CPC ............ *A61B 5/4088* (2013.01); *A61B 3/113* (2013.01); *A61B 3/14* (2013.01); *A61B 5/163* (2017.08); *A61B 5/7282* (2013.01); *G06T 7/248* (2017.01); *G06V 10/56* (2022.01); *G06V 40/193* (2022.01); *G06V 40/20* (2022.01); *A61B 5/7267* (2013.01); *G06T 2207/30196* (2013.01)

(58) Field of Classification Search
CPC ......... A61B 5/4088; A61B 3/113; A61B 3/14; A61B 5/163; A61B 5/7282; A61B 5/7267; G06T 7/248; G06T 2207/30196; G06V 10/56; G06V 40/193; G06V 40/20
See application file for complete search history.

(56) References Cited

U.S. PATENT DOCUMENTS

| | | | |
|---|---|---|---|
| 10,685,748 B1 * | 6/2020 | Chappell | G16H 10/20 |
| 2016/0106315 A1 * | 4/2016 | Kempinski | G16H 50/20 |
| | | | 351/210 |
| 2023/0052100 A1 * | 2/2023 | Devani | A61B 3/1216 |

FOREIGN PATENT DOCUMENTS

| | | | |
|---|---|---|---|
| JP | 2005-143599 A | 6/2005 | |
| KR | 1357493 B1 * | 2/2014 | |
| KR | 10-2019-0135908 A | 12/2019 | |
| KR | 10-2155309 B1 | 9/2020 | |
| KR | 102494464 B1 * | 12/2020 | ........... A61B 5/4088 |

* cited by examiner

*Primary Examiner* — Serkan Akar
(74) *Attorney, Agent, or Firm* — Aird & McBurney LP

(57) ABSTRACT

Disclosed is a method of identifying dementia by at least one processor of a device. The method includes performing a first task that causes a first object to be displayed on a first region of a screen displayed on a user terminal; and when a preset condition is satisfied, performing a second task that causes at least one object, which induces the user's gaze, to be displayed instead of the first object on the screen of the user terminal.

15 Claims, 8 Drawing Sheets

IDENTIFYING A DEMENTIA BASED ON GAZE INFORMATION OF USER PERFORMING TASK ON A SCREEN AND GAZE TASK SCORE

CROSS-REFERENCE TO RELATED APPLICATIONS

This application claims benefit of priority to Korean Patent Application No. 10-2022-0008986 filed Jan. 21, 2022, the entire contents of which are incorporated herein by reference.

TECHNICAL FIELD

The present disclosure relates to a technique of identifying dementia, more particularly to a device for identifying dementia using user's gaze information according to tests and a method thereof.

BACKGROUND ART

Alzheimer's disease (AD), which is a brain disease caused by aging, causes progressive memory impairment, cognitive deficits, changes in individual personality, etc. In addition, dementia refers to a state of persistent and overall cognitive function decline that occurs when a person who has led a normal life suffers from damage to brain function due to various causes. Here, cognitive function refers to various intellectual abilities such as memory, language ability, temporal and spatial understanding ability, judgment ability, and abstract thinking ability. Each cognitive function is closely related to a specific part of the brain. The most common form of dementia is Alzheimer's disease.

Various methods have been proposed for diagnosing Alzheimer's disease, dementia, or mild cognitive impairment. For example, a method of diagnosing Alzheimer's disease or mild cognitive impairment using the expression level of miR-206 in the olfactory tissue, a method for diagnosing dementia using a biomarker that characteristically increases in blood, and the like are known.

However, since special equipment or tests necessary for biopsy are required so as to use miR-206 in the olfactory tissue, and blood from a patient should be collected by an invasive method so as to use biomarkers in blood, there is a disadvantage that the patient's rejection feeling is relatively large.

Therefore, there is an urgent need for development of a dementia diagnosis method where patients hardly feel rejection without a separate special equipment or examination.

DISCLOSURE

Technical Problem

The present disclosure has been made in view of the above problems, and it is one object of the present disclosure to provide an accurate dementia diagnosis method where patients hardly feel rejection.

It will be understood that technical problems of the present disclosure are not limited to the aforementioned problem and other technical problems not referred to herein will be clearly understood by those skilled in the art from the description below.

Technical Solution

In accordance with an aspect of the present disclosure, the above and other objects can be accomplished by the provision of a method of identifying dementia by at least one processor of a device, the method including: performing a first task that causes a first object to be displayed on a first region of a screen displayed on a user terminal; and when a preset condition is satisfied, performing a second task that causes at least one object, which induces the user's gaze, to be displayed instead of the first object on the screen of the user terminal.

In accordance with some embodiments of the present disclosure, the method may further include performing the first task and the second task a preset number of times.

In accordance with some embodiments of the present disclosure, the method may further include: acquiring gaze information related to the user while the second task is performed the preset number of times; calculating the score by inputting the gaze information into a dementia identification model; and determining whether a user has dementia based on the score.

In accordance with some embodiments of the present disclosure, the gaze information may be generated by, after the device receives an image containing user's eye from the user terminal while the second task is performed the preset number of times, analyzing the image by the device.

In accordance with some embodiments of the present disclosure, the gaze information may be information received from the user terminal by the device, and may be generated by analyzing the image containing the user's eye by the user terminal while the second task is performed the preset number of times.

In accordance with some embodiments of the present disclosure, the gaze information may include at least one of the information on the number of times that the user correctly performed the preset gaze task, information on the number of times the user failed to perform the preset gaze task correctly, the information on whether user's gaze continues to stare at a specific point for a preset time, information on a time elapsed from a time point when a screen including the at least one object is displayed to a time point when the user's gaze moves to any one of the at least one objects, information on a movement speed of the user's gaze, and information on whether the user's gaze is accurately staring at a point related to the preset gaze task.

In accordance with some embodiments of the present disclosure, the at least one object may include text displayed instead of the first object on the first region; and a second object and third object respectively displayed in a second region and third region different from the first region, wherein the first region is located between the second region and the third region, and the preset gaze task includes at least one of a task to stare at an object related to a meaning of the text among the second object and the third object; a task to stare at an object not related to a meaning of the text among the second object and the third object; a task to stare at an object related to a color of the text among the second object and the third object; and a task to stare at an object not related to a color of the text among the second object and the third object.

In accordance with some embodiments of the present disclosure, the at least one object may include a gaze-inducing object displayed in any one area of a second region and third region different from the first region, wherein the first region is located between the second region and the third region, and the preset gaze task includes at least one of a task to stare at the gaze-inducing object; and a task to stare at in a direction opposite to a direction in which the gaze-inducing object is located.

In accordance with some embodiments of the present disclosure, the preset condition may be satisfied when it is recognized that the user is staring at the first object for a preset time by analyzing an image acquired while the first task is performed.

In accordance with some embodiments of the present disclosure, the preset condition may be satisfied when it is recognized that a central point position of the user's pupil exists within a preset region.

In accordance with some embodiments of the present disclosure, a size of the preset region may be determined according to a size of the user's pupil.

In accordance with some embodiments of the present disclosure, the preset condition may be satisfied when the coordinate value of the user's pupil has a preset coordinate value for a preset time.

In accordance with another aspect of the present invention, there is provided, a computer program stored on a computer-readable storage medium, wherein the computer program, when executed on at least one processor of a device, performs processes of identifying dementia, the processes including: a process of performing a first task causing a first object to be displayed on a first region of a screen displayed on a user terminal; and when a preset condition is satisfied, a process of performing a second task causing at least one object, which induces the user's gaze, to be displayed instead of the first object on the screen of the user terminal.

In accordance with yet another aspect of the present invention, there is provided A device for identifying dementia, the device including: a storage configured to store at least one program instruction; and at least one processor configured to execute the at least one program instruction, wherein the at least one processor performs a first task causing a first object to be displayed on a first region of a screen displayed on a user terminal and, when a preset condition is satisfied, performs a second task causing at least one object, which induces the user's gaze, to be displayed instead of the first object on the screen of the user terminal.

The technical solutions obtainable in the present disclosure are not limited to the above-mentioned solutions, and other solutions that are not mentioned can be clearly understood by those of ordinary skill in the art, to which the present disclosure belongs, from the description below.

Advantageous Effects

The effect of a technique of identifying dementia according to the present disclosure is as follows.

According to some embodiments of the present disclosure, provided is an accurate dementia diagnosis method where patients hardly feel rejection.

It will be understood that effects obtained by the present disclosure are not limited to the aforementioned effect and other effects not referred to herein will be clearly understood by those skilled in the art from the description below.

DESCRIPTION OF DRAWINGS

Various embodiments of the present disclosure are described with reference to the accompanying drawings. Here, like reference numbers are used to refer to like elements. In the following embodiments, numerous specific details are set forth so as to provide a thorough understanding of one or more embodiments for purposes of explanation. It will be apparent, however, that such embodiment (s) may be practiced without these specific details.

BEST MODE

Figure 1:
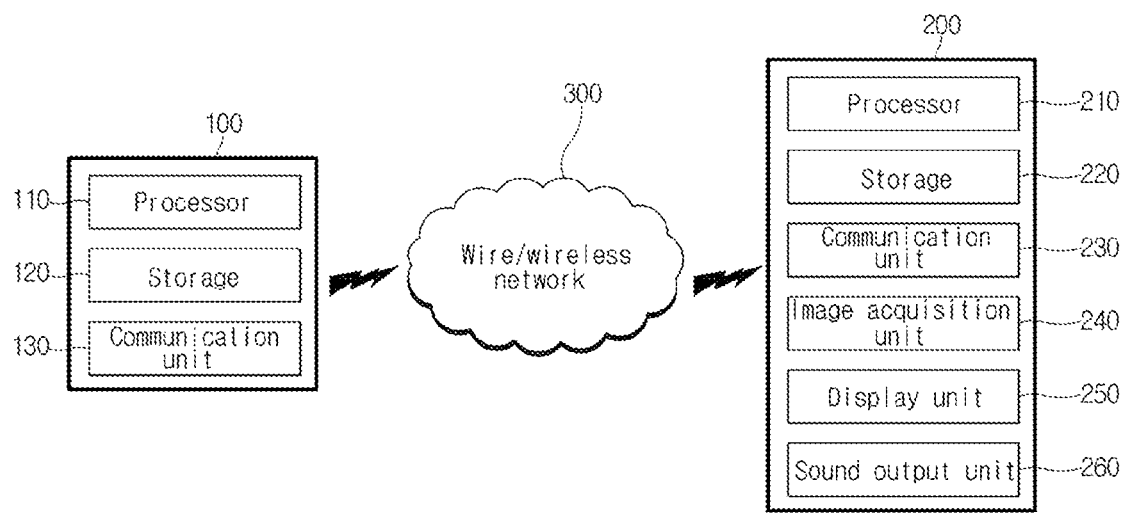
FIG. 1 is a schematic diagram for explaining a system for identifying dementia according to some embodiments of the present disclosure.

Hereinafter, various embodiments of an apparatus according to the present disclosure and a method of controlling the same will be described in detail with reference to the accompanying drawings. Regardless of the reference numerals, the same or similar components are assigned the same reference numerals, and overlapping descriptions thereof will be omitted.

Objectives and effects of the present disclosure, and technical configurations for achieving the objectives and the effects will become apparent with reference to embodiments described below in detail in conjunction with the accompanying drawings. In describing one or more embodiments of the present disclosure, a detailed description of known functions and configurations incorporated herein will be omitted when it may make the subject matter of the present disclosure unclear.

The terms used in the specification are defined in consideration of functions used in the present disclosure, and can be changed according to the intent or conventionally used methods of clients, operators, and users. The features of the present disclosure will be more clearly understood from the accompanying drawings and should not be limited by the accompanying drawings, and it is to be appreciated that all changes, equivalents, and substitutes that do not depart from the spirit and technical scope of the present disclosure are encompassed in the present disclosure.

The suffixes "module" and "unit" of elements herein are used for convenience of description and thus can be used interchangeably and do not have any distinguishable meanings or functions.

Terms including an ordinal number, such as first, second, etc., may be used to describe various elements, but the elements are not limited by the terms. The above terms are used only for the purpose of distinguishing one component from another component. Therefore, a first component mentioned below may be a second component within the spirit of the present description.

A singular expression includes a plural expression unless the context clearly dictates otherwise. That is, a singular expression in the present disclosure and in the claims should generally be construed to mean "one or more" unless specified otherwise or if it is not clear from the context to refer to a singular form.

The terms such as "include" or "comprise" may be construed to denote a certain characteristic, number, step, operation, constituent element, or a combination thereof, but may not be construed to exclude the existence of or a possibility of addition of one or more other characteristics, numbers, steps, operations, constituent elements, or combinations thereof.

The term "or" in the present disclosure should be understood as "or" in an implicit sense and not "or" in an exclusive sense. That is, unless otherwise specified or clear from context, "X employs A or B" is intended to mean one of natural implicit substitutions. That is, when X employs A; when X employs B; or when X employs both A and B, "X employs A or B" can be applied to any one of these cases. Furthermore, the term "and/or" as used in the present disclosure should be understood to refer to and encompass all possible combinations of one or more of listed related items.

As used in the present disclosure, the terms "information" and "data" may be used interchangeably.

Unless otherwise defined, all terms (including technical and scientific terms) used in the present disclosure may be used with meanings that can be commonly understood by those of ordinary skill in the technical field of the present disclosure. Also, terms defined in general used dictionary are not to be excessively interpreted unless specifically defined However, the present disclosure is not limited to embodiments disclosed below and may be implemented in various different forms. Some embodiments of the present disclosure are provided merely to fully inform those of ordinary skill in the technical field of the present disclosure of the scope of the present disclosure, and the present disclosure is only defined by the scope of the claims. Therefore, the definition should be made based on the content throughout the present disclosure.

According to some embodiments of the present disclosure, at least one processor (hereinafter, referred to as a "processor") of the device may determine whether a user has dementia using a dementia identification model. Specifically, the processor may acquire a score value by acquiring user's gaze information and then, inputting the gaze information into the dementia identification model. In addition, the processor may determine whether the user has dementia based on the score value. Hereinafter, a method of identifying dementia is described with reference to FIGS. 1 to 8.

FIG. 1 is a schematic diagram for explaining a system for identifying dementia according to some embodiments of the present disclosure.

Referring to FIG. 1, the system for identifying dementia may include a device 100 for identifying dementia and a user terminal 200 for a user requiring dementia identification. In addition, the device 100 and the user terminal 200 may be connected to communication through the wire/wireless network 300. However, the components constituting the system shown in FIG. 1 are not essential in implementing the system for identifying dementia, and thus more or fewer components than those listed above may be included.

The device 100 of the present disclosure may be paired with or connected to the user terminal 200 through the wire/wireless network 300, thereby transmitting/receiving predetermined data. have. In this case, data transmitted/received through the wire/wireless network 300 may be converted before transmission/reception. Here, the "wire/wireless network" 300 collectively refers to a communication network supporting various communication standards or protocols for pairing and/or data transmission/reception between the device 100 and the user terminal 200. The wire/wireless network 300 includes all communication networks to be supported now or in the future according to the standard and may support all of one or more communication protocols for the same.

The device 100 for identifying dementia may include a processor 110, a storage 120, and a communication unit 130. The components shown in FIG. 1 are not essential for implementing the device 100, and thus, the device 100 described in the present disclosure may include more or fewer components than those listed above.

Each component of the device 100 of the present disclosure may be integrated, added, or omitted according to the specifications of the device 100 that is actually implemented. That is, as needed, two or more components may be combined into one component or one component may be subdivided into two or more components. In addition, a function performed in each block is for explaining an embodiment of the present disclosure, and the specific operation or device does not limit the scope of the present disclosure.

The device 100 described in the present disclosure may include any device that transmits and receives at least one of data, content, service, and application, but the present disclosure is not limited thereto.

The device 100 of the present disclosure includes, for example, any standing devices such as a server, a personal computer (PC), a microprocessor, a mainframe computer, a digital processor and a device controller; and any mobile devices (or handheld device) such as a smart phone, a tablet PC, and a notebook, but the present disclosure is not limited thereto.

In the present disclosure, the term "server" refers to a device or system that supplies data to or receives data from various types of user terminals, i.e., a client.

For example, a web server or portal server that provides a web page or a web content (or a web service), an advertising server that provides advertising data, a content server that provides content, an SNS server that provides a Social Network Service (SNS), a service server provided by a manufacturer, a Multichannel Video Programming Distributor (MVPD) that provides Video on Demand (VoD) or a streaming service, a service server that provides a pay service, or the like may be included as a server.

In the present disclosure, the device 100 means a server according to context, but may mean a fixed device or a mobile device, or may be used in an all-inclusive sense unless specified otherwise.

The processor 110 may generally control the overall operation of the device 100 in addition to an operation related to an application program. The processor 110 may provide or process appropriate information or functions by processing signals, data, information, etc. that are input or output through the components of the device 100 or driving an application program stored in the storage 120.

The processor 110 may control at least some of the components of the device 100 to drive an application program stored in the storage 120. Furthermore, the processor 110 may operate by combining at least two or more of the components included in the device 100 to drive the application program.

The processor 110 may include one or more cores, and may be any of a variety of commercial processors. For example, the processor 110 may include a Central Processing Unit (CPU), General Purpose Graphics Processing Unit (GPUGP), Tensor Processing Unit (TPU), and the like of the device. However, the present disclosure is not limited thereto.

The processor 110 of the present disclosure may be configured as a dual processor or other multiprocessor architecture. However, the present disclosure is not limited thereto.

The processor 110 may identify whether a user has dementia using the dementia identification model according to some embodiments of the present disclosure by reading a computer program stored in the storage 120.

The storage 120 may store data supporting various functions of the device 100. The storage 120 may store a plurality of application programs (or applications) driven in the device 100, and data, commands, and at least one program command for the operation of the device 100. At least some of these application programs may be downloaded from an external server through wireless communication. In addition, at least some of these application programs may exist in the device 100 from the time of shipment for basic functions of the device 100. Meanwhile, the application program may be stored in the storage 120, installed in the device 100, and driven by the processor 110 to perform the operation (or function) of the device 100.

The storage 120 may store any type of information generated or determined by the processor 110 and any type of information received through the communication unit 130.

The storage 120 may include at least one type of storage medium of a flash memory type, a hard disk type, a Solid State Disk (SSD) type, a Silicon Disk Drive (SDD) type, a multimedia card micro type, a card-type memory (e.g., SD memory, XD memory, etc.), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk. The device 100 may be operated in relation to a web storage that performs a storage function of the storage 120 on the Internet.

The communication unit 130 may include one or more modules that enable wire/wireless communication between the device 100 and a wire/wireless communication system, between the device 100 and another device, or between the device 100 and an external server. In addition, the communication unit 130 may include one or more modules that connect the device 100 to one or more networks.

The communication unit 130 refers to a module for wired/wireless Internet connection, and may be built-in or external to the device 100. The communication unit 130 may be configured to transmit and receive wire/wireless signals.

The communication unit 130 may transmit/receive a radio signal with at least one of a base station, an external terminal, and a server on a mobile communication network constructed according to technical standards or communication methods for mobile communication (e.g., Global System for Mobile communication (GSM), Code Division Multi Access (CDMA), Code Division Multi Access 2000 (CDMA2000), Enhanced Voice-Data Optimized or Enhanced Voice-Data Only (EV-DO), Wideband CDMA (WCDMA), High Speed Downlink Packet Access (HSDPA), High Speed Uplink Packet Access (HSUPA), Long Term Evolution (LTE), Long Term Evolution-Advanced (LTE-A), etc.).

An example of wireless Internet technology includes Wireless LAN (WLAN), Wireless-Fidelity (Wi-Fi), Wireless Fidelity (Wi-Fi) Direct, Digital Living Network Alliance (DLNA), Wireless Broadband (WiBro), World Interoperability for Microwave Access (WiMAX), High Speed Downlink Packet Access (HSDPA), High Speed Uplink Packet Access (HSUPA), Long Term Evolution (LTE), Long Term Evolution-Advanced (LTE-A), and the like. However, in a range including Internet technologies not listed above, the communication unit 130 may transmit/receive data according to at least one wireless Internet technology.

In addition, the communication unit 130 may be configured to transmit and receive signals through short range communication. The communication unit 130 may perform short range communication using at least one of Bluetooth™, Radio Frequency Identification (RFID), Infrared Data Association (IrDA), Ultra-Wideband (UWB), ZigBee, Near Field Communication (NFC), Wireless-Fidelity (Wi-Fi), Wi-Fi Direct and Wireless Universal Serial Bus (Wireless USB) technology. The communication unit 130 may support wireless communication through short range communication networks (wireless area networks). The short range communication networks may be wireless personal area networks.

The device 100 according to some embodiments of the present disclosure may be connected to the user terminal 200 and the wire/wireless network 300 through the communication unit 130.

In the present disclosure, the user terminal 200 may be paired with or connected to the device 100, in which the dementia identification model is stored, through the wire/wireless network 300, thereby transmitting/receiving and displaying predetermined data.

The user terminal 200 described in the present disclosure may include any device that transmits, receives, and displays at least one of data, content, service, and application. In addition, the user terminal 200 may be a terminal of a user who wants to check dementia. However, the present disclosure is not limited thereto.

In the present disclosure, the user terminal 200 may include, for example, a mobile device such as a mobile phone, a smart phone, a tablet PC, or an ultrabook. However, the present disclosure is not limited thereto, and the user terminal 200 may include a standing device such as a Personal Computer (PC), a microprocessor, a mainframe computer, a digital processor, or a device controller.

The user terminal 200 includes a processor 210, a storage 220, a communication unit 230, an image acquisition unit 240, a display unit 250, and a sound output unit 260. The components shown in FIG. 1 are not essential in implementing the user terminal 200, and thus, the user terminal 200 described in the present disclosure may have more or fewer components than those listed above.

Each component of the user terminal 200 of the present disclosure may be integrated, added, or omitted according to the specifications of the user terminal 200 that is actually implemented. That is, as needed, two or more components may be combined into one component, or one component may be subdivided into two or more components. In addition, the function performed in each block is for explaining an embodiment of the present disclosure, and the specific operation or device does not limit the scope of the present disclosure.

Since the processor 210, storage 220 and communication unit 230 of the user terminal 200 are the same components as the processor 210, storage 220 and communication unit 230 of the user terminal 200, a duplicate description will be omitted, and differences therebetween are mainly described below.

In the present disclosure, the processor 210 of the user terminal 200 may control the display unit 250 such that a first object is displayed on a first region of the screen before displaying a screen for identifying whether a user has dementia. In addition, the user terminal 200 may control the display unit 250 such that at least one object that induces movement of the user's gaze is displayed instead of the first object when a preset condition is satisfied. This is described in more detail below with reference to FIG. 2.

Meanwhile, since high processing speed and computational power are required to perform an operation using the dementia identification model, the dementia identification model may be stored only in the storage 120 of the device 100 and may not be stored in the storage 220 of the user terminal 200. However, the present disclosure is not limited thereto.

The image acquisition unit 240 may include one or a plurality of cameras. That is, the user terminal 200 may be a device including one or plural cameras provided on at least one of a front part and rear part thereof.

The image acquisition unit 240 may process an image frame, such as a still image or a moving image, obtained by an image sensor. The processed image frame may be displayed on the display unit 250 or stored in the storage 220. Meanwhile, the image acquisition unit 240 provided in the user terminal 200 may match a plurality of cameras to form a matrix structure. A plurality of image information having various angles or focuses may be input to the user terminal 200 through the cameras forming the matrix structure as described above.

The image acquisition unit 240 of the present disclosure may include a plurality of lenses arranged along at least one line. The plurality of lenses may be arranged in a matrix form. The plural lenses may be arranged in a matrix form. Such cameras may be called an array camera. When the image acquisition unit 240 is configured as an array camera, images may be captured in various ways using the plural lenses, and images of better quality may be acquired.

According to some embodiments of the present disclosure, the image acquisition unit 240 may acquire an image including the user's eyes of the user terminal in association with display of a specific screen on the user terminal 200.

The display unit 250 may display (output) information processed by the user terminal 200. For example, the display unit 250 may display execution screen information of an application program driven in the user terminal 200, or User Interface (UI) and Graphic User Interface (GUI) information according to the execution screen information.

The display unit 250 may include at least one of a Liquid Crystal Display (LCD), a Thin-Film Transistor-Liquid Crystal Display (TFT LCD), an Organic Light-Emitting Diode (OLED), a flexible display, a 3(d) display, an e-ink display. However, the present disclosure is not limited thereto.

According to some embodiments of the present disclosure, the display unit 250 may display a first object (e.g., cross-shaped object) on the first region of the screen when the first task is performed. In addition, the display unit 250 may display at least one object of inducing movement of the user's gaze instead of the first object on the first region of the screen when the second task is performed.

The sound output unit 260 may output audio data (or sound data, etc.) received from the communication unit 230 or stored in the storage 220. The sound output unit 260 may also output a sound signal related to a function performed by the user terminal 200.

The sound output unit 260 may include a receiver, a speaker, a buzzer, and the like. That is, the sound output unit 260 may be implemented as a receiver or may be implemented in the form of a loudspeaker. However, the present disclosure is not limited thereto.

According to some embodiments of the present disclosure, the sound output unit 260 may output a preset sound (e.g., a voice describing what a user should perform through a first task or a second task) in connection with performing the first task or the second task. However, the present disclosure is not limited thereto.

According to some embodiments of the present disclosure, the device 100 may determine whether a user has dementia by acquiring an image including the user's eye received from the user terminal 200. However, since the user terminal 200 is not a fixed terminal, it is necessary to go through a special task when acquiring an image. Hereinafter, a task for acquiring an image including the user's eye is described with reference to FIG. 2.

Figure 2:
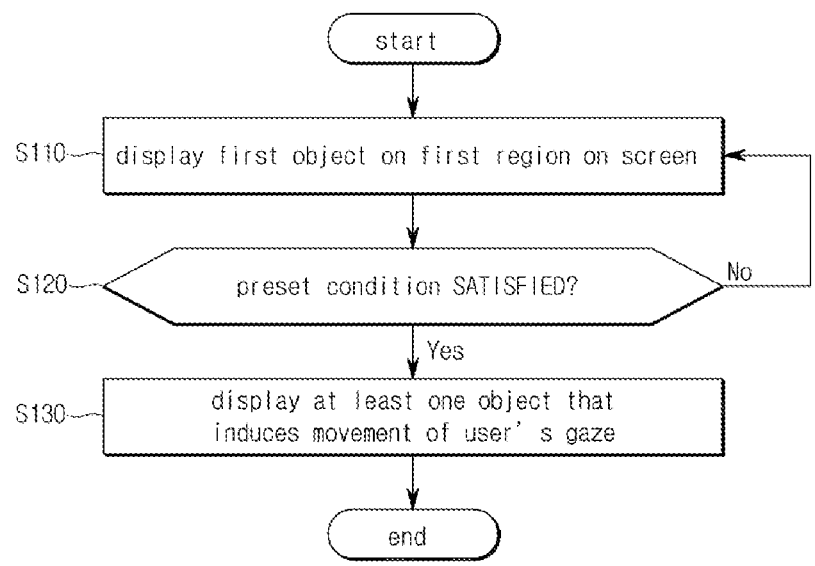
FIG. 2 is a flowchart for explaining an embodiment of a method of acquiring an image for dementia identification by a device according to some embodiments of the present disclosure.
Figure 3:
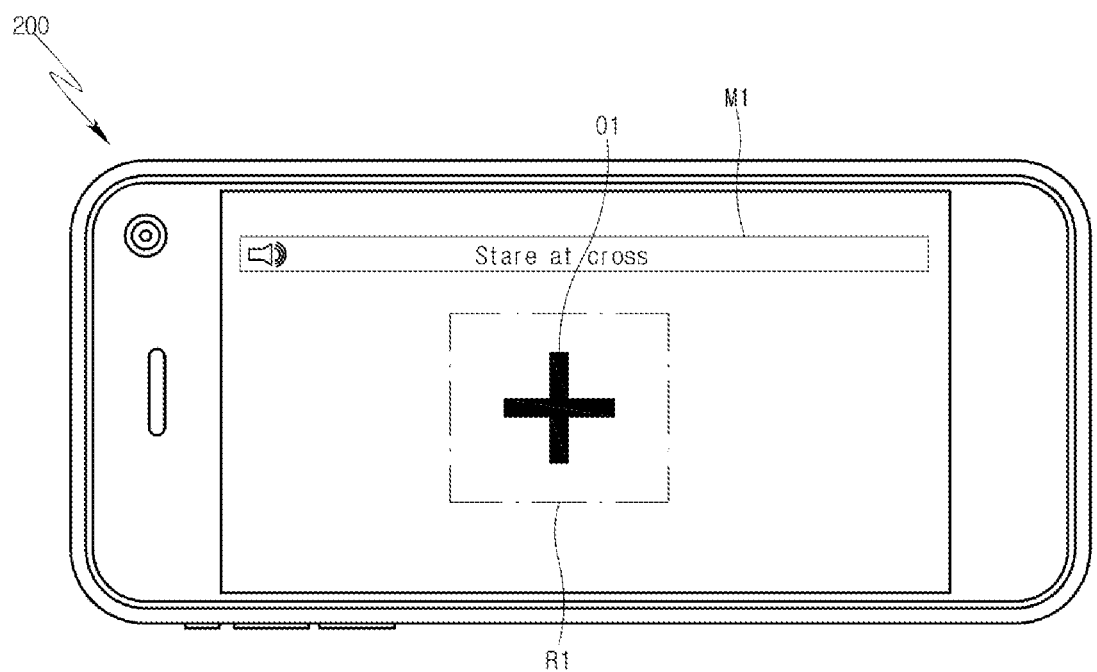
FIG. 3 is a diagram for explaining an example of a screen displayed when acquiring an image for dementia identification in a user terminal according to some embodiments of the present disclosure.
Figure 4:
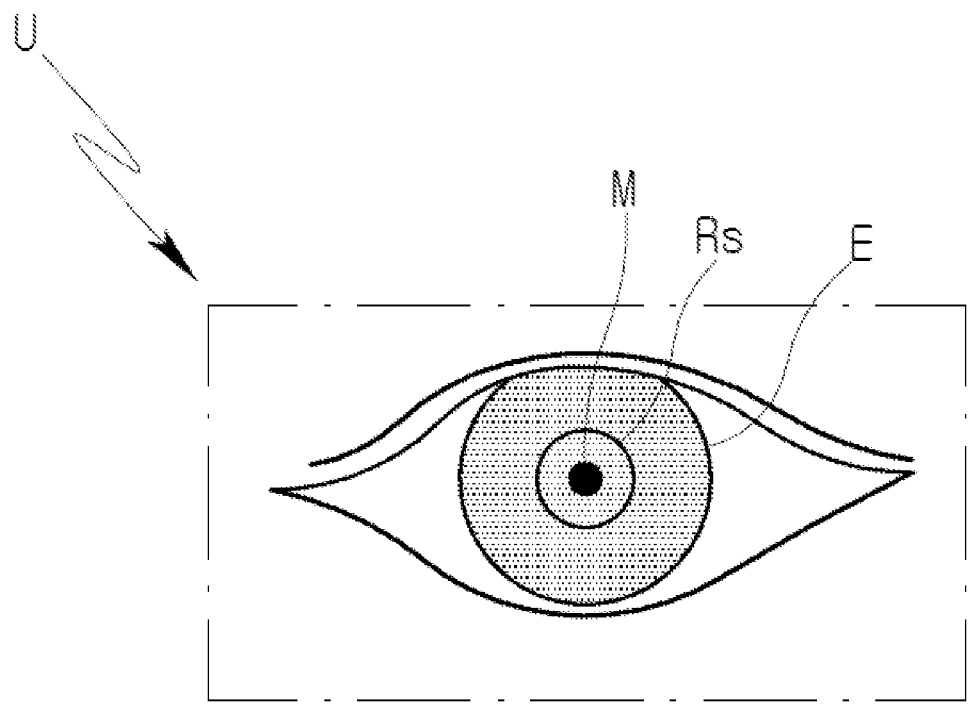
FIG. 4 is a diagram for explaining an embodiment of a method of recognizing whether a user of a user terminal satisfies a preset condition according to some embodiments of the present disclosure.
Figure 5:
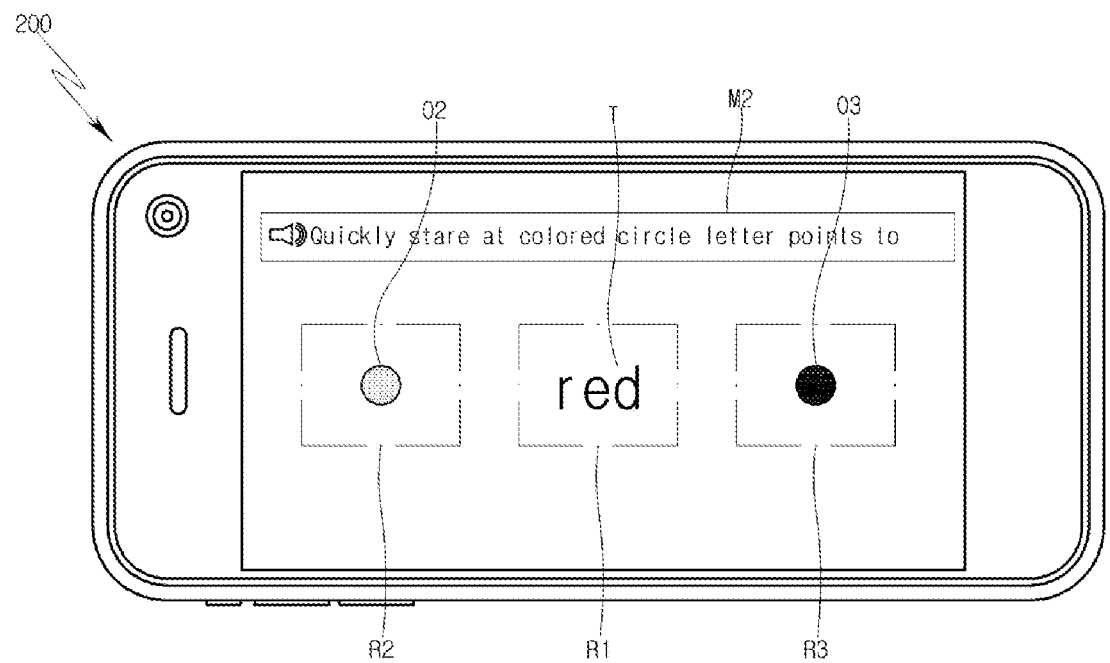
FIGS. 5 to 6B are diagrams for explaining examples of screens displayed when acquiring gaze information in a user terminal according to some embodiments of the present disclosure.

FIG. 2 is a flowchart for explaining an embodiment of a method of acquiring an image for dementia identification by a device according to some embodiments of the present disclosure. FIG. 3 is a diagram for explaining an example of a screen displayed when acquiring an image for dementia identification in a user terminal according to some embodiments of the present disclosure. FIG. 4 is a diagram for explaining an embodiment of a method of recognizing whether a user of a user terminal satisfies a preset condition according to some embodiments of the present disclosure. FIGS. 5 to 6B are diagrams for explaining examples of screens displayed when acquiring gaze information in a user terminal according to some embodiments of the present disclosure. In describing FIGS. 2 to 6B, the contents overlapping with those described above in relation to FIG. 1 are not described again, and differences therebetween are mainly described below.

Referring to FIG. 2, the processor 110 of the device 100 may perform a first task causing a first object to be displayed on the first region of the screen displayed on the user terminal 200 (S110).

For example, the processor 110 of the device 100 may generate a screen including the first object on the first region and may transmit the generated screen to the user terminal 200. In this case, the user terminal 200 may display a screen containing the first object on the first region.

As another example, the screen including the first object on the first region may be stored in the storage 220 of the user terminal 200. When the processor 210 of the user terminal 200 receives a signal to display the screen stored in the storage 220 from the device 100 through the communication unit 230, the processor 210 may control the display unit 250 to display the screen on the user terminal 200.

As still another example, the image of a first object may be stored in the storage 220 of the user terminal 200. In this case, when the processor 110 of the device 100 transmits a signal to display the screen including the first object to the user terminal 200 through the communication unit 230, the processor 210 of the user terminal 200 may create and display the screen including the first object on the first region.

However, since the above-described examples are merely examples, the present disclosure is not limited to the above-described examples.

Referring to FIG. 3, a screen displayed on the user terminal 200 may include a first object O1 in a first region R1.

The first object O1 may be an object that induces the user's gaze to come to the center of the displayed screen. For example, the first object O1 may be an object having a cross shape. However, the first object O1 is not limited to the above-described example and may have various shapes or shapes.

The first region R1 may be a region located at the exact center of the screen. Thus, the user's gaze staring at the first object O1 may come to the center of the screen. However, the present invention is not limited thereto.

Meanwhile, according to some embodiments of the present disclosure, a message M1 of the content informing the user of the task to be performed through a currently displayed screen may be displayed on a screen displayed on the user terminal 200. For example, the message M1 may include content to look at the first object O1 currently being displayed on the screen. In addition, the user terminal 200 may output a sound (e.g., a voice explaining the contents contained in the message M1) related to the message M1 through the sound output unit 260 in conjunction with displaying the message M1 on the screen through the display unit 250. In this way, when a sound is output together with the message M1 to notify the user of a task to be performed by the user, the user can clearly understand what needs to be done now. Thus, the chance of doing a wrong thing by simple mistake may be lowered.

Referring to FIG. 2 again, when the first object is displayed on the first region of the screen in S110), the processor 110 of the device 100 may check whether the preset condition is satisfied (S120).

For example, the user terminal 200 may acquire an image including the user's eye of the user terminal through the image acquisition unit 240 in conjunction with displaying (performing the first task) the first object O1 on the first region (R1) of the displayed screen. Whether the preset condition is satisfied may be checked by analyzing the image in the user terminal 200. In addition, when the user terminal 200 recognizes that the preset condition is satisfied, the processor 210 of the user terminal 200 may transmit the signal that the preset condition is satisfied to the device 100 through the communication unit 230. In this case, the device 100 may recognize that the preset condition is satisfied.

As another example, the user terminal 200 may acquire an image including user's eye of the user's terminal through the image acquisition unit 240 in conjunction with displaying (performing the first task) the first object O1 on the first region (R1) of the displayed screen. The user terminal 200 may control the communication unit 230 to transmit the acquired image to the device 100. When the processor 110 of the device 100 receives the image including the user's eye through the communication unit 230, the processor may analyze the image to determine whether the preset condition is satisfied.

However, the above-described examples are only examples and the present disclosure is not limited to the above-described examples.

The preset condition may be satisfied when a first user stares at the first object for a preset time by analyzing the image acquired while the first task is being performed (that is, while the first object O1 is being displayed on the first region R1).

For example, referring to FIG. 4, the preset condition may be satisfied when it is recognized that the central point M position of the user's U pupil E exists within the preset area Rs for a preset time. Here, the preset region Rs may correspond to a region, in which the central point M of the pupil E of the user U can be located, when the user's eye stares at the exact center of the display unit 250.

Specifically, the processor 110 of the device 100 may determine the location of the user's U pupil E in each of a plurality of frames by using only a B value among respective RGB values of the plural frames included in the acquired image. That is, the processor 110 may recognize that a region having a B value exceeding a preset threshold value in each of the plural frames is a region where the pupil E is located. In addition, the processor 110 may recognize that the preset condition is satisfied when it is recognized that the position of the center point of the region where the pupil E is located is within the preset region Rs. However, the present invention is not limited thereto, and the above-described method of confirming the position of the pupil E may be performed by the processor 210 of the user terminal 200.

As another example, the preset condition may be satisfied when the coordinate value of the pupil E of the user has the preset coordinate value for the preset time. Here, the coordinate value of the pupil E may be the coordinate value of the central point M of the pupil E or may be the coordinate values of the edge of the pupil E. In addition, the preset coordinate value may be a coordinate value at which the pupil E is located when the user stares at the center of the display unit 250 of the user terminal 200. However, the present invention is not limited thereto.

According to some embodiments of the present disclosure, the processor 110 may distinguish the pupil E from the background in the acquired image. In addition, the processor 110 may undergo a binarization process of changing a part corresponding to the position of the pupil E to black and a part corresponding to the background to white. In addition, the processor 110 may apply a flood fill to remove noise after the binarization process. Here, the flood fill may refer to an operation of replacing white pixels surrounded by black pixels with black pixels and replacing black pixels surrounded with white pixels. Next, the processor 110 may recognize whether the position of the central point of the pupil is located within the preset region Rs using the acquired image.

According to some embodiments of the present disclosure, the size of the preset region Rs may be determined according to the size of the pupil E. Since the size of the pupil E may be different for each user, accuracy may be improved by determining whether a preset condition is satisfied if the size of the preset region Rs is changed according to the size of the pupil.

More specifically, when an image including the user U's eye is acquired, the processor 110 may analyze the image to recognize the size of the pupil E. In addition, the processor 110 may determine the size of the preset region Rs based on the size of the pupil E. The size of the preset region Rs may be proportional to the size of the pupil E. In addition, the size of the preset region Rs may be smaller than the size of the pupil E.

According to some embodiments of the present disclosure, the processor 210 of the user terminal 200 may acquire an image including the user's eye by activating the image acquisition unit 240 while the screen including the first object O1 is displayed. In this case, the processor 210 may check whether the user's eye is included in the image. If the processor 210 recognizes that the user's eye is not included in the image, the processor 210 may control the display unit 250 to display the screen, in which the first object O1 is located on the first region R, while continuing to acquire the image. However, the present invention is not limited thereto.

Referring to FIG. 2 again, when the processor 110 of the device 100 recognizes that the preset condition is not satisfied (S120, No), the processor may cause the first object to be continuously displayed on the first region of the screen displayed on the user terminal 200 (S110).

Meanwhile, when the device 100 recognizes that the preset condition is satisfied (S120, Yes), the processor 110 of the device 100 may perform the second task causing the user terminal 200 to display at least one object that induces movement of the user's gaze instead of the first object on the screen (S130).

The processor 110 of the device 100 which is an example related to S130 may perform a sub-task causing the user terminal 200 to display a screen including a second object, a third object, and text. In this case, the user terminal 200 may display the second object and the third object in the second area and the third area, respectively, in conjunction with displaying the text, instead of the first object, on the first region. That is, at least one object may include text displayed instead of the first object on the first region, and second and third objects respectively displayed on second and third regions different from the first region.

More specifically, referring to FIG. 5, if the preset condition is satisfied, a screen displayed on the user terminal 200 may include text (T) instead of the first object (O1 in FIG. 3) in the first region R1, and a second object O2 and third object O3 respectively included in the second region R2 and third region R3 different from the first region R1. Here, the screen including the second object O2, the third object O3, and the text T may be displayed for 2000 ms, without being limited thereto.

The second object O2 and the third object O3 may have the same shape (e.g., a circular shape with a diameter of 0.2 cm, etc.) and only have different colors. In this case, any one of the second object O2 and the third object O3 may have a color indicated by the text T, and the other object may have a color different from the color indicated by the text T. However, the present invention is not limited thereto, and the second object O2 and the third object O3 may have different shapes and different colors.

The first region R1 may be located between the second region R2 and the third region R3. That is, the second region R2 and the third region R3 may be located on both sides of the first region R1 positioned in the center. However, the present invention is not limited thereto.

The text T may be a word meaning color or shape. However, the meaning of the text T is not limited to the above-described example.

If the meaning of the text T is related to color, the color of the text T itself may be the same as or different from the color that the text T means. However, the present invention is not limited thereto.

Meanwhile, according to some embodiments of the present disclosure, the message M2 of a content indicating what a preset gaze task that a user should perform is displayed may be displayed on a screen displayed on the user terminal 200. Here, the preset gaze task may indicate which object a user should stare at.

According to some embodiments, the preset gaze task may be a task for staring at an object related to the meaning of the text T among the second object O2 and the third object O3. In this case, the meaning of the text T may be related to shape or color. However, the meaning of the text T is not limited to the above-described example.

For example, the text T may mean red, the second object O2 may have red, and the third object O3 may have blue. In addition, the message M2 displayed on the screen may include the content to stare at the object of the color indicated by the text T. In this case, when a user stares at the second object O2, it may be considered that the user performs the preset task correctly.

As another example, although not shown in the drawing, the text T may mean a circle, the second object O2 may have a circular shape, and the third object O3 may have a rectangular shape. In addition, a message M2 displayed on the screen may include the content to stare at an object having a shape indicated by the text T. In this case, when a user stares at the second object O2, it may be considered that the user performs the preset task correctly.

According to some other embodiments, the preset gaze task may be a task to stare at an object unrelated to the meaning of the text T among the second object O2 and the third object O3. In this case, the meaning of the text T may be related to shape or color. However, the meaning of the text T is not limited to the above-described example.

For example, the text T may mean red, the second object O2 may have red, and the third object O3 may have blue. In addition, the message M2 displayed on the screen may include a content to stare at an object that does not have a color indicated by the text T. In this case, if a user stares at the third object O3, it may be considered that the user performs the preset task correctly.

As another example, the text T may mean a circle, the second object O2 may have a circular shape, and the third object O3 may have a rectangular shape. In addition, the message M2 displayed on the screen may include a content to stare at an object that does not have a shape indicated by the text T. In this case, if a user stares at the third object O3, it may be considered that the user performs the preset task correctly.

According to some other embodiments, the preset gaze task may be a task to stare at an object related to the color of the text T itself among the second object O2 and the third object O3. In this case, the color of the text T itself may be different from the meaning of the text T, or may be the same as the meaning of the text T.

For example, the text T may mean red, the text T may be red, the second object O2 may have red, and the third object O3 may have blue. In addition, the message M2 displayed on the screen may include a content to stare at an object having the color of the text T. In this case, if a user stares at the second object O2, it may be considered that the user performs the preset task correctly.

As another example, the text T may mean red, the color of the text T may be blue different from the meaning of the text T, the second object O2 may have red, and the third object O3 may have blue. In addition, the message M2 displayed on the screen may include a content to stare at an object having the color of the text T. In this case, if a user stares at the third object O3, it may be considered that the user performs the preset task correctly.

According to some other embodiments, the preset gaze task may be a task to stare at an object unrelated to the color of the text T itself among the second object O2 and the third object O3. In this case, the color of the text T itself may be different from the meaning of the text T, or may be the same as the meaning of the text T.

For example, the text T may mean red, the text T may be red, the second object O2 may have red, and the third object O3 may have blue. In addition, the message M2 displayed on the screen may include a content to stare at an object that does not have the color of the text T. In this case, if a user stares at the third object O3, it may be considered that the user performs the preset task correctly.

As another example, the text T may mean red, the color of the text T may be blue different from the meaning of the text T, the second object O2 may have red, and the third object O3 may have blue. In addition, the message M2 displayed on the screen may include a content to stare at an object that does not have the color of the text T. In this case, if a user stares at the second object O2, it may be considered that the user performs the preset task correctly.

Meanwhile, the user terminal 200 may output a sound (e.g., a voice explaining the content contained in the message M2) related to the message M2 through the sound output unit 260 in conjunction with displaying the message M2 on the screen through the display unit 250. In this way, when a user is recognized with a preset gaze task that the user should perform with a sound together with the message M2, the user can clearly understand what the preset gaze task that the user should currently perform is. Therefore, the possibility of performing a wrong gaze task by simple mistake may be lowered.

As a result, the preset gaze task may include at least one of a task to stare at an object related to the meaning of the text among the second object and the third object, a task to stare at an object not related to the meaning of the text among the second object and the third object, a task to stare at an object related to the color of the text among the second object and the third object, and a task to stare at an object not related to the color of the text among the second object and the third object. In addition, the message M2 displayed on the screen may include information on what the preset gaze task is.

As another example related to step S130, the processor 110 of the device 100 may perform a sub-task causing the user terminal 200 to display a gaze-inducing object in any one of the second and third regions different from the first region. In this case, the user terminal 200 may display a gaze-inducing object in the second or third region different from the first region instead of displaying the first object. That is, at least one object may include a gaze-inducing object displayed in any one of the second region and third region different from the first region.

Figure 6A:
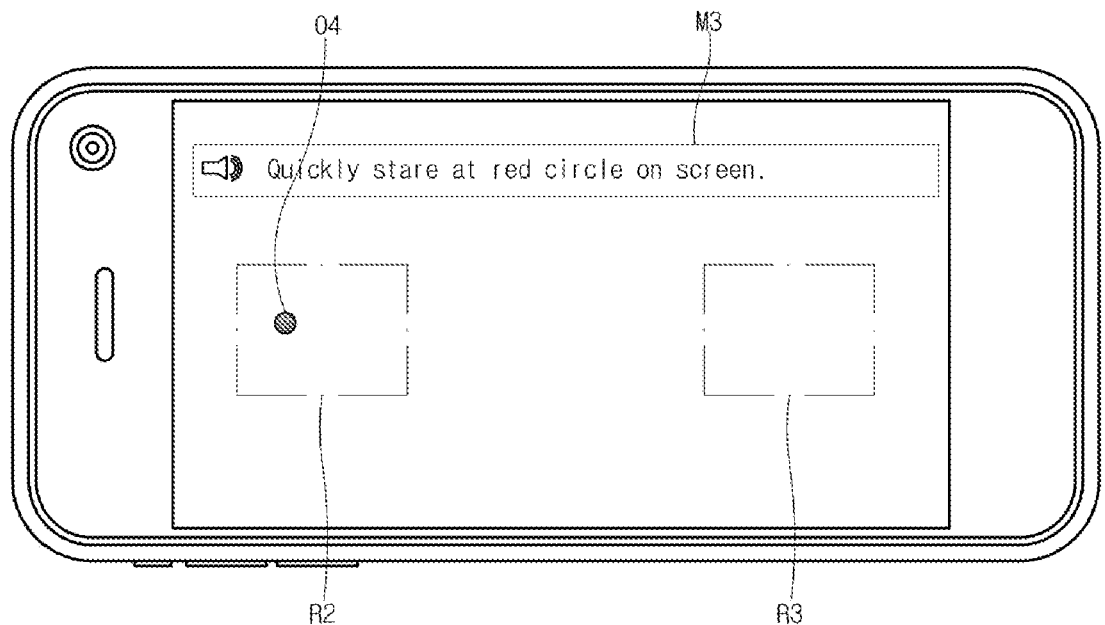
Figure 6B:
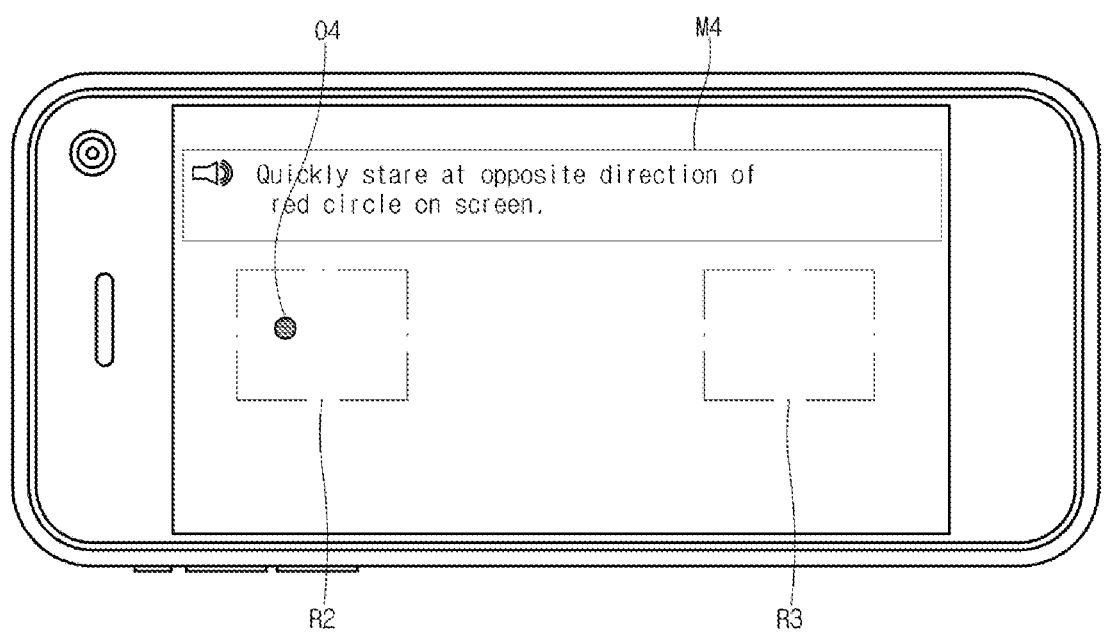

More specifically, referring to FIGS. 6A and 6B, a screen displayed on the user terminal 200 may include a gaze-inducing object O4 displayed in any one area R2 among the second region R2 and third region R3 different from the first region R1 in FIG. 3 when the preset condition is satisfied. Here, any one of the second region R2 and the third region R3 may be randomly selected, and a screen including the gaze-inducing object O4 may be displayed for 2000 ms. However, the present invention is not limited thereto.

The gaze-inducing object O4 may be an object having a preset shape (e.g., a circular shape with a diameter of 0.2 cm, etc.) and a preset color (e.g., red).

The first region R1 may be located between the second region R2 and the third region R3. That is, the second region R2 and the third region R3 may be located on both sides of the first region R1 positioned in the center. However, the present invention is not limited thereto.

Meanwhile, according to some embodiments of the present disclosure, a message (M3, M4) of a content informing a preset gaze task that a user should perform may be displayed on a screen displayed on the user terminal 200. Here, the preset gaze task may indicate which object the user should stare at.

Referring to FIG. 6A, the preset gaze task may be a task to stare at the gaze-inducing object O4. In addition, a message M3 displayed on the screen may include a content to quickly stare at the gaze-inducing object O4. In this case, if a user stares at the gaze-inducing object O4, it may be considered that the user performs the preset task correctly.

Referring to FIG. 6B, the preset gaze task may be a task to stare at in an opposite direction to the direction in which the gaze-inducing object O4 is located. In addition, the message M4 displayed on the screen may include a content to quickly stare at the gaze-inducing object O4. In this case, if a user stares at any point in an opposite direction to the gaze-inducing object O4, it may be considered that the user performs the preset task correctly.

Meanwhile, the user terminal 200 may output a sound (e.g., a voice explaining the content contained in the message M3 or M4) related to the message M3 or M4 through the sound output unit 260 in conjunction with displaying the message M3 or M4 on the screen through the display unit 250. In this way, when a user is recognized with a preset gaze task that the user should perform with a sound together with the message M3 or M4, the user can clearly understand what the preset gaze task that the user should currently perform is. Therefore, the possibility of performing a wrong gaze task by simple mistake may be lowered.

As a result, the preset gaze task may include at least one of a task to stare at a gaze-inducing object and a task to stare at in a direction opposite to the direction in which a gaze-inducing object is positioned. In addition, the message M3 or M4 displayed on the screen may include information on what the preset gaze task is.

Referring FIG. 2 again, the processor 110 of the device 100 may perform the first task and the second task a preset number of times (e.g., 5 times). That is, when the processor 110 causes the screen shown in FIG. 3 to be displayed on the user terminal 200 and then the user's gaze is recognized to stare at the center, a task to cause the screen shown in FIGS. 5 to 6B to be displayed on the user terminal 200 may be performed a preset number of times.

When the user's gaze is centered by performing the first task before proceeding with testing (i.e., before performing the second task) as in the present disclosure, dementia may be accurately identified even if the user does not add a separate component to the user terminal 200 that the user is using.

Meanwhile, when a non-dementia patient has to stare at an object displayed on the left or right side of the screen without staring at the center, the gaze cannot move quickly, so the person who does not have dementia may be determined to have dementia. Therefore, the accuracy of dementia identification may be improved when a user stares at the center and then stares at an object displayed on the left or right side of the screen. Thus, the present disclosure suggests that a screen with a first object in the center is displayed such that a user can stare at the center before performing the second task.

Meanwhile, according to some embodiments of the present disclosure, the processor 110 of the device 100 may acquire gaze information related to the user while the second task is performed a preset number of times. Here, the gaze information may be used as a digital biomarker (a biomarker obtained from a digital device) to identify dementia.

For example, the processor 210 of the user terminal 200 may acquire an image including the user's eye while the second task is performed a preset number of times. In this case, the processor 110 of the device 100 may receive an image including the user's eye from the user terminal 200 through the communication unit 230 while the second task is performed a preset number of times. When the processor 110 receives the image, the processor 110 may analyze the image to generate gaze information.

As another example, the processor 210 of the user terminal 200 may acquire an image including the user's eye while the second task is performed a preset number of times. The processor 210 may acquire gaze information by analyzing the acquired image. In addition, the processor 210 may control the communication unit 230 to transmit the acquired gaze information to the device 100. In this case, the processor 110 of the device 100 may receive gaze information from the user terminal 200 through the communication unit 230.

The gaze information may include at least one of information on the number of times that a user correctly performed a preset gaze task, information on the number of times a user failed to perform a preset gaze task correctly, information on whether the user's gaze continues to stare at a specific point for a preset time, information on the time elapsed from the time when a screen including at least one object is displayed to the time when the user's gaze moves to any one of the at least one object (information on a delay time of a user's response), information on a movement speed of the user's gaze, and information on whether the user's gaze is accurately staring at a point related to a preset gaze task.

The gaze information of the present disclosure may be a digital biomarker with a high correlation coefficient with dementia identification among various types of digital biomarkers. Therefore, when determining whether a user has dementia using gaze information, the accuracy of dementia identification may be improved.

According to some embodiments of the present disclosure, the processor 110 may perform a preliminary task so that a user can check the preset gaze task prior to performing the first task and the second task. Here, since the preliminary task proceeds in the same manner as the above-described first task and the second task, a detailed description thereof is omitted.

The gaze information obtained in the preliminary task may not be used to identify whether a user has dementia through the dementia identification model. However, the present invention is not limited thereto, and the gaze information obtained through the preliminary task may also be input into the dementia identification model so as to increase the dementia identification accuracy in the dementia identification model.

Meanwhile, according to some embodiments of the present disclosure, the processor 110 may determine whether a user has dementia by using gaze information when the gaze information is obtained. A detailed description thereof is described below with reference to FIG. 7.

Figure 7:
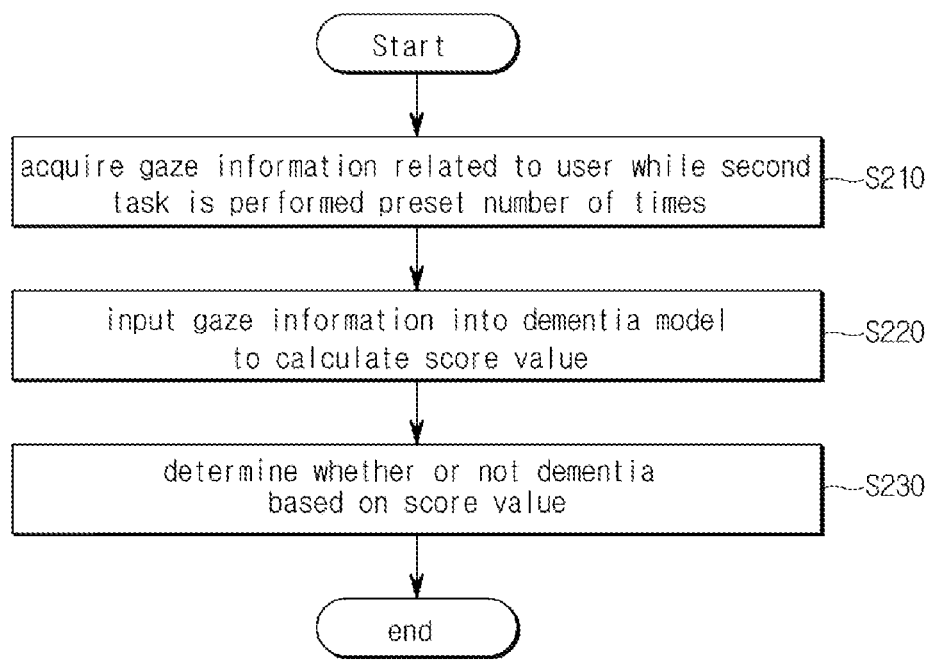
FIG. 7 is a flowchart for explaining an embodiment of a method of determining whether a user has dementia using gaze information by a device according to some embodiments of the present disclosure.
Figure 8:
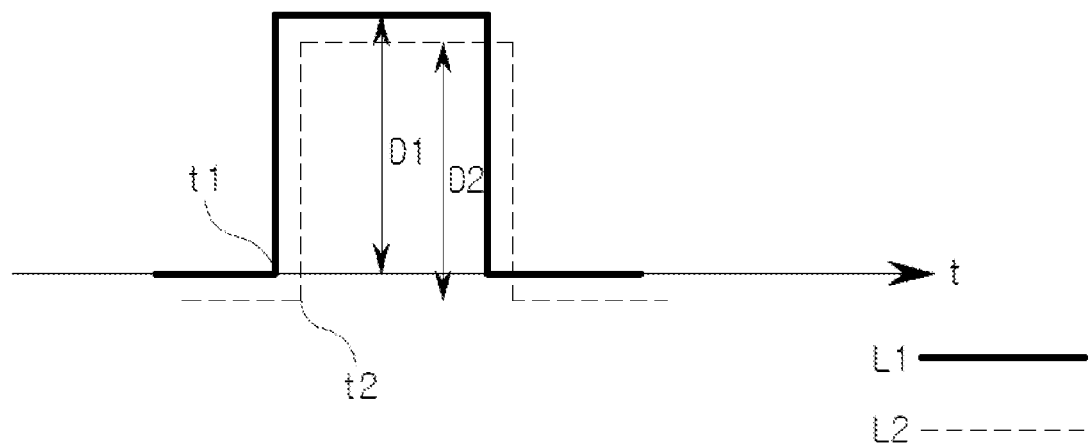
FIG. 8 is a diagram for explaining an embodiment of a method of obtaining gaze information according to some embodiments of the present disclosure.

FIG. 7 is a flowchart for explaining an embodiment of a method of determining whether a user has dementia using gaze information by a device according to some embodiments of the present disclosure. FIG. 8 is a diagram for explaining an embodiment of a method of obtaining gaze information according to some embodiments of the present disclosure. In describing FIG. 7 and FIG. 8, the contents overlapping with those described above in relation to FIGS. 1 to 6B are not described and differences therebetween are mainly described below.

Referring to FIG. 7, the processor 110 of the device 100 may acquire gaze information related to a user while the second task is performed a preset number of times (S210).

Specifically, the processor 110 may recognize a pupil by analyzing an image including the user's eye while performing the second task a preset number of times. The processor 110 may calculate a coordinate value of the pupil after recognizing the pupil. The coordinate value of the pupil may be a coordinate value of a central point of the pupil, or may be coordinate values of the entire pupil. In the present disclosure, the gaze information may be generated using the coordinate value of the pupil.

The gaze information may include at least one of information on the number of times that a user correctly performed a preset gaze task, information on the number of times a user failed to perform a preset gaze task correctly, information on whether the user's gaze continues to stare at a specific point for a preset time, information on a time elapsed from the time when a screen including at least one object is displayed to the time when the user's gaze moves to any one of the at least one object, information on a movement speed of the user's gaze, and information on whether the user's gaze is accurately staring at a point related to a preset gaze task. However, the present invention is not limited thereto, and the gaze information may include less or more information than the above-described information. In addition, gaze information may include all of the above information so as to improve dementia.

According to some embodiments of the present disclosure, when the first task and the second task are performed a preset number of times, the processor 110 may calculate the number of times the user correctly performs the preset gaze task and the number of times the user fails to correctly perform the preset gaze task from the preset number of times.

The information on whether the user's gaze continues to stare at a specific point for a preset time may be calculated based on whether the user's pupil moves at a specific position at a specific point.

For example, the information on whether the user's gaze continues to stare at a specific point for a preset time may be calculated based on whether the user's pupil moves at a specific location while the first object is being displayed. Here, the specific position may be a position where the pupil is located when staring the first object, and it may be determined that the pupil has moved when the coordinate value of the pupil is out of a preset critical range.

As another example, the information on whether the user's gaze continues to stare at a specific point for a preset time may be calculated based on whether the user's pupil does not move and stops for a preset time at a last stop position after the user's pupil moves. Here, the specific position may be a position where the pupil is located when staring at the second object O2 or third object O3 of FIG. 5 or the gaze-inducing object O4 of FIGS. 6A and 6B, and when the coordinate value of the pupil is out of a preset critical range, it may be determined that the pupil has moved.

Since a dementia patient cannot stare at one point for a long time, the accuracy of dementia identification may be improved by acquiring information on whether the user's gaze continues to stare at a specific point for a preset time is acquired and using the information as a digital biomarker for dementia identification.

Meanwhile, the method of acquiring information included in gaze information is described more specifically as follows with reference to FIG. 8.

In FIG. 8, the x-axis is an axis related to time, and the y-axis may be an axis related to a distance moved by the gaze or to a distance from the center of the screen to an object stared by a user. In addition, a first line L1 is a line representing a distance from the center of a screen to an object that a user should stare over time, and a second line L2 may be a line representing a distance by which the user's gaze moves over time.

In the present disclosure, a method of acquiring gaze information when the screen described with reference to FIG. 5 is displayed is described below.

In the present disclosure, a first time point t1 may be a time point at which a screen including text, a second object, and a third object is displayed.

In addition, after the screen including text, the second object, and the third object is displayed, the time when the user's gaze starts to move to the second object or the third object may be a second time point t2. Here, the second time point t2 may be a time point when the coordinates of the pupil start to move in a stationary state. However, the present invention is not limited thereto.

In the present disclosure, a delayed time of a user's response may mean a time elapsed from the first time point t1, when a screen containing the second object and the third object is displayed, to the second time point t2 when the user's gaze moves to the second object or the third object.

Meanwhile, information on whether the user's gaze is accurately staring at the point (i.e., the second object or the third object) associated with the preset gaze task may be calculated using the distance D2 by which the user's gaze moves and the distance D1 from the text (T) to a point related to the preset gaze task (the second object O2 or the third object O3, an object the user should stare at). Here, the distance D2 by which the user's gaze has moved may be calculated using an initial coordinate value of the pupil (a coordinate value at the point where the pupil is located before the pupil moves) and a final coordinate value of the pupil (a coordinate value at a last point where the pupil stops after moving).

Specifically, information (i.e., information on whether the user is properly staring at an object that should be stared) on whether the user's gaze is accurately staring at the point (the second object or the third object) related to the preset gaze task may be calculated using a value obtained by dividing the second distance D2 by the first distance D1. Here, as the value approaches 1, it may be considered that the user's gaze accurately stares at the point (the second object or the third object) related to the preset gaze task.

Meanwhile, a method of acquiring gaze information when the screen shown in FIGS. 6A and 6B is displayed is described below.

In the present disclosure, the first time point t1 may be a time when a screen including a gaze-inducing object is displayed.

In addition, the second time point t2 may be a time the user's gaze starts to move after the screen including the gaze-inducing object is displayed. Here, the second time point t2 may be a point in time when the coordinates of the pupil start to move in a stationary state. However, the present invention is not limited thereto.

In the present disclosure, the delay time of a user's response is a time taken from the first time point t1, when a screen containing a gaze-inducing object is displayed, to the second time point t2, when the user's gaze moves.

Meanwhile, information on whether the user's gaze is accurately staring at a point related to a preset gaze task may be calculated using the distance D2 where the user's gaze moves and the distance D1 from the first area R1 to a point (a point at which the user should stare) related to the preset gaze task. Here, the distance D2 where the user's gaze moves may be calculated using an initial coordinate value (coordinate value at a point where the pupil is located before the pupil moves) of the pupil and a final coordinate value of the pupil (a coordinate value at a last point where the pupil stops after moving).

Specifically, information (i.e., information on whether the user is properly staring at an object that needs to be stared) on whether the user's gaze is accurately staring at a gaze-inducing object or an arbitrary point on an opposite side of the gaze-inducing object may be calculated using a value obtained by dividing the second distance D2 by the first distance D1. Here, as the value approaches 1, it may be considered that the user's gaze is accurately staring at a point related to the preset gaze task.

In the present disclosure, a movement velocity of the user's gaze may be calculated by differentiating the position trajectory shown in FIG. 8 and reducing the velocity value. However, the present invention is not limited thereto, and the movement velocity may be calculated based on information on a distance where the user's eye moves from the center to a target point and information on a time taken when the user's eye moves from the center to the target point. The processor 110 may calculate the movement velocity of the user's gaze in various ways.

Meanwhile, referring to FIG. 7 again, when the processor 110 acquires gaze information in S210, the processor 110 may input the gaze information into the dementia identification model to calculate a score value (S220). Here, the dementia identification model may refer to an artificial intelligence model having a neural network structure previously learned to calculate a score value when gaze information is input. In addition, the score value may mean a value that can recognize whether a user has dementia.

According to some embodiments of the present disclosure, a pre-learned dementia identification model may be stored in the storage 120 of the device 100.

The dementia identification model may be trained by a method of updating the weight of a neural network by back propagating a difference value between label data labeled in learning data and prediction data output from the dementia identification model.

In the present disclosure, the training data may be gaze information obtained by performing the above-described first task and second task by a plurality of test users through their test devices.

In the present disclosure, the test users may include a user classified as a patient with mild cognitive impairment, a user classified as an Alzheimer's patient, a user classified as normal, and the like. However, the present disclosure is not limited thereto.

In the present disclosure, the test device may refer to a device where various test users perform tests when securing learning data. Here, the test device may be a mobile device such as a mobile phone, a smart phone, a tablet PC, an ultrabook, etc., similarly to the user terminal 200 used for dementia identification. However, the present disclosure is not limited thereto.

In the present disclosure, the label data may be a score value capable of recognizing whether a patient is normal, is an Alzheimer's patient, and a patient with mild cognitive impairment. However, the present disclosure is not limited thereto.

A dementia identification model may be composed of a set of interconnected computational units, which may generally be referred to as nodes. These nodes may also be referred to as neurons. The neural network may be configured to include at least one node. Nodes (or neurons) constituting the neural network may be interconnected by one or more links.

In the dementia identification model, one or more nodes connected through a link may relatively form a relationship between an input node and an output node. The concepts of an input node and an output node are relative, and any node in an output node relationship with respect to one node may be in an input node relationship in a relationship with another node, and vice versa. As described above, an input node-to-output node relationship may be created around a link. One output node may be connected to one input node through a link, and vice versa.

In the relation between the input node and the output node connected through one link, a value of data of the output node may be determined based on data that is input to the input node. Here, the link interconnecting the input node and the output node may have a weight. The weight may be variable, and may be changed by a user or an algorithm so as for the neural network to perform a desired function.

For example, when one or more input nodes are connected to one output node by each link, the output node may determine an output node value based on values that are input to input nodes connected to the output node and based on a weight set in a link corresponding to each input node.

As described above, in the dementia identification model, one or more nodes may be interconnected through one or more links to form an input node and output node relationship in the neural network. The characteristics of the dementia identification model may be determined according to the number of nodes and links in the dementia identification model, a correlation between nodes and links, and a weight value assigned to each of the links.

The dementia identification model may consist of a set of one or more nodes. A subset of nodes constituting the dementia identification model may constitute a layer. Some of the nodes constituting the dementia identification model may configure one layer based on distances from an initial input node. For example, a set of nodes having a distance of n from the initial input node may constitute n layers. The distance from the initial input node may be defined by the minimum number of links that should be traversed to reach the corresponding node from the initial input node. However, the definition of such a layer is arbitrary for the purpose of explanation, and the order of the layer in the dementia identification model may be defined in a different way from that described above. For example, a layer of nodes may be defined by a distance from a final output node.

The initial input node may refer to one or more nodes to which data (i.e., at least one of gaze information, result data obtained by performing the third task, and information on user's response time) is directly input without going through a link in a relationship with other nodes among nodes in the neural network. Alternatively, in a relationship between nodes based on a link in the dementia identification model, it may mean nodes that do not have other input nodes connected by a link. Similarly, the final output node may refer to one or more nodes that do not have an output node in relation to other nodes among nodes in the neural network. In addition, a hidden node may refer to nodes constituting the neural network other than the first input node and the last output node.

In the dementia identification model according to some embodiments of the present disclosure, the number of nodes in the input layer may be greater than the number of nodes in the output layer, and the neural network may have a form wherein the number of nodes decreases as it progresses from the input layer to the hidden layer. In addition, information on the number of times that a user correctly performed a preset gaze task, information on the number of times a user failed to perform a preset gaze task correctly, information on whether the user's gaze continues to stare at a specific point for a preset time, information on a time elapsed from a time point when a screen including the at least one object is displayed to a time point when the user's gaze moves to any one of the at least one objects, information on a movement speed of the user's gaze, and information on whether the user's gaze is accurately staring at a point related to the preset gaze task may be inputted in each node of the input layer. However, the present invention is not limited thereto.

According to some embodiments of the present disclosure, the dementia identification model may have a deep neural network structure.

A Deep Neural Network (DNN) may refer to a neural network including a plurality of hidden layers in addition to an input layer and an output layer. DNN may be used to identify the latent structures of data.

DNN may include convolutional neural networks (CNNs), Recurrent Neural Networks (RNNs), auto encoders, Generative Adversarial Networks (GANs), and a Restricted Boltzmann Machines (RBM), a Deep Belief Network (DBN), a Q network, a U network, a Siamese network, a Generative Adversarial Network (GAN), and the like. These DNNs are only provided as examples, and the present disclosure is not limited thereto.

The dementia identification model of the present disclosure may be learned in a supervised learning manner. However, the present disclosure is not limited thereto, and the dementia identification model may be learned in at least one manner of unsupervised learning, semi supervised learning, or reinforcement learning.

Learning of the dementia identification model may be a process of applying knowledge for performing an operation of identifying dementia by the dementia identification model to a neural network.

The dementia identification model may be trained in a way that minimizes errors in output. Learning of the dementia identification model is a process of repeatedly inputting learning data (test result data for learning) into the dementia identification model, calculating errors of an output (score value predicted through the neural network) and target (score value used as label data) of the dementia identification model on the learning data, and updating the weight of each node of the dementia identification model by back-propagating the error of the dementia identification model from an output layer of the dementia identification model to an input layer in a direction of reducing the error.

A change amount of a connection weight of each node to be updated may be determined according to a learning rate. Calculation of the dementia identification model on the input data and backpropagation of errors may constitute a learning cycle (epoch). The learning rate may be differently applied depending on the number of repetitions of a learning cycle of the dementia identification model. For example, in an early stage of learning the dementia identification model, a high learning rate may be used to enable the dementia identification model to quickly acquire a certain level of performance, thereby increasing efficiency, and, in a late stage of learning the dementia identification model, accuracy may be increased by using a low learning rate.

In the learning of the dementia identification model, the learning data may be a subset of actual data (i.e., data to be processed using the learned dementia identification model), and thus, there may be a learning cycle wherein errors for learning data decrease but errors for real data increase. Overfitting is a phenomenon wherein errors on actual data increase due to over-learning on learning data as described above.

Overfitting may act as a cause of increasing errors in a machine learning algorithm. To prevent such overfitting, methods such as increasing training data; regularization; and dropout that deactivate some of nodes in a network during a learning process, and utilization of a batch normalization layer may be applied.

Meanwhile, when a score value is acquired through step S220, the processor 110 may determine whether dementia is present based on the score value (S230).

Specifically, the processor 110 may determine whether dementia is present based on whether the score value exceeds a preset threshold value.

For example, the processor 110 may determine that a user has dementia when recognizing that the score value output from the dementia identification model exceeds the preset threshold value.

As another example, the processor 110 may determine that a user does not have dementia when recognizing that the score value output from the dementia identification model is less than or equal to the preset threshold value.

The above-described embodiments are only provided as examples, and the present disclosure is not limited to the embodiments.

According to some embodiments of the present disclosure, the processor 110 of the device 100 may acquire user identification information before proceeding with the above-described first task and second task. Here, the user identification information may include user's age information, gender information, name, address information, etc. In addition, at least a portion of the user identification information may be used as input data for the dementia identification model together with gaze information. Specifically, age information and gender information may be used as input data for the dementia identification model together with gaze information. In this way, when at least a portion of the user identification information is used together with the gaze information and is input to the dementia identification model to obtain a score value and identify whether or not dementia is present, the accuracy of dementia identification may be further improved. In this case, the dementia identification model may be a model wherein learning is completed based on at least a part of user identification information, and gaze information.

120 people in a cognitive normal group and 9 people in a cognitively impaired group conducted an experiment to identify whether they had dementia through their user terminal. The goal of this experiment was to confirm the accuracy of the pre-learned dementia identification model. Specifically, the device 100 discriminated whether a user has dementia based on the score value generated by inputting the gaze information obtained by performing the first task and the second task into the dementia identification model of the present disclosure. It was confirmed that the classification accuracy calculated through the above-described experiment was 80% or more.

According to at least one of the above-described several embodiments of the present disclosure, dementia may be accurately diagnosed in a method in which a patient hardly feels rejection.

In the present disclosure, the configurations and methods of the above-described several embodiments of the device 100 are not limitedly applied, and all or parts of each of the embodiments may be selectively combined to allow various modifications.

Various embodiments described in the present disclosure may be implemented in a computer or similar device-readable recording medium using, for example, software, hardware, or a combination thereof.

According to hardware implementation, some embodiments described herein may be implemented using at least one of Application Specific Integrated Circuits (ASICs), Digital Signal Processors (DSPs), Digital Signal Processing Devices (DSPDs), Programmable Logic Devices (PLDs), Field Programmable Gate Arrays (FPGAs), processors, controllers, micro-controllers, microprocessors, and other electrical units for performing functions. In some cases, some embodiments described in the present disclosure may be implemented with at least one processor.

According to software implementation, some embodiments such as the procedures and functions described in the present disclosure may be implemented as separate software modules. Each of the software modules may perform one or more functions, tasks, and operations described in the present disclosure. A software code may be implemented as a software application written in a suitable programming language. Here, the software code may be stored in the storage 120 and executed by at least one processor 110. That is, at least one program command may be stored in the storage 120, and the at least one program command may be executed by the at least one processor 110.

The method of identifying dementia by the at least one processor 110 of the device 100 using the dementia identification model according to some embodiments of the present disclosure may be implemented as code readable by the at least one processor in a recording medium readable by the at least one processor 110 provided in the device 100. The at least one processor-readable recording medium includes all types of recording devices in which data readable by the at least one processor 110 is stored. Examples of the at least one processor-readable recording medium includes Read Only Memory (ROM), Random Access Memory (RAM), CD-ROM, a magnetic tape, a floppy disk, an optical data storage device, and the like.

Meanwhile, although the present disclosure has been described with reference to the accompanying drawings, this is only an embodiment and the present disclosure is not limited to a specific embodiment. Various contents that can be modified by those of ordinary skill in the art to which the present disclosure belongs also belong to the scope of rights according to the claims. In addition, such modifications should not be understood separately from the technical spirit of the present disclosure.

The invention claimed is:

1. A method of identifying dementia of a user, the method comprising:
performing a first task by at least one processor of a device that causes a first object configured to be displayed on a first region of a screen displayed on a user terminal configured to induce the user's gaze of the user terminal to stare at the first region;
causing at least one camera of the user terminal by the at least one processor to acquire an image of the user's eye while the first task is performed;
recognizing by the at least one processor, by analyzing the image of the user's eye acquired while the first task is performed, that the user is staring at the first object for a preset time by recognizing that a central point position of the user's pupil exists within a preset region for the preset time, wherein the preset region corresponds to a region in which the central point position of the user's pupil is located when the user's eye stares at a center of the screen, and wherein the image comprises a plurality of pixels;

after recognizing that the user has stared at the first object for the preset time, performing a second task by the at least one processor that causes at least one object, which induces the user's gaze to move to a region of the screen other than the first region, instead of the first object on the screen of the user terminal, configured to be displayed in the region of the screen other than the first region, wherein the first task and the second task are performed a preset number of times;

causing by the at least one processor the at least one camera of the user terminal to acquire another image of the user's eye while the second task is performed the preset number of times;

by analyzing, by the at least one processor, the another image of the user's eye, generating gaze information related to the user while the second task is performed the preset number of times; wherein the gaze information comprises at least one of information on a number of times that the user correctly performed a preset gaze task, information on a number of times the user failed to perform the preset gaze task correctly, information on whether the user's gaze continues to stare at a specific point for the preset time, information on a time elapsed from a time point that a screen comprising the at least one object is displayed to a time point that the user's gaze moves to any one of the at least one object, information on a movement speed of the user's gaze, and information on whether the user's gaze is accurately staring at a point related to the preset gaze task;

calculating, by the at least one processor, a score by inputting the gaze information into a dementia identification model; and determining, by the at least one processor, whether the user has dementia based on the score;

wherein either:
(a) the at least one object comprises: text displayed instead of the first object on the first region; and a second object and third object respectively displayed in a second region and third region different from the first region;
the first region is located between the second region and the third region, and
the preset gaze task comprises at least one of: a task to stare at an object related to a meaning of the text among the second object and the third object; and a task to stare at an object related to a color of the text among the second object and the third object; or
(b) the at least one object comprises a gaze-inducing object displayed in any one area of a second region and third region different from the first region; and
the first region is located between the second region and the third region, and
the preset gaze task comprises a task to stare in a direction opposite to a direction in which the gaze-inducing object is located.

2. The method according to claim 1, wherein the gaze information is generated after the device receives the another image of the user's eye.

3. The method according to claim 1, wherein the gaze information is information received from the user terminal by the device.

4. The method according to claim 1, wherein the at least one object comprises: the text displayed instead of the first object on the first region; and the second object and the third object respectively displayed in the second region and the third region different from the first region;
wherein the first region is located between the second region and the third region; and
wherein the preset gaze task comprises at least one of: the task to stare at the object related to the meaning of the text among the second object and the third object; and the task to stare at the object related to the color of the text among the second object and the third object.

5. The method according to claim 1, wherein the at least one object comprises the gaze-inducing object displayed in any one area of the second region and the third region different from the first region; and
wherein the first region is located between the second region and the third region; and
wherein the preset gaze task comprises the task to stare in the direction opposite to the direction in which the gaze-inducing object is located.

6. The method according to claim 1, wherein a size of the preset region is determined according to a size of the user's pupil.

7. The method according to claim 1, wherein recognizing that the user is staring at the first object for the preset time comprises recognizing that a coordinate value of the user's pupil has a preset coordinate value for the preset time.

8. A computer program stored on a computer-readable storage medium, wherein the computer program, when executed on at least one processor of a device, the at least one processor performs processes of identifying dementia of a user, the processes comprising:

a process of performing a first task causing a first object configured to be displayed on a first region of a screen displayed on a user terminal configured so as to induce the user's gaze of the user terminal to stare at the first region;

a process of causing at least one camera of the user terminal to acquire an image of the user's eye while the first task is performed;

a process of recognizing, by analyzing the image of the user's eye acquired while the first task is performed, that the user is staring at the first object for a preset time by recognizing that a central point position of the user's pupil exists within a preset region, wherein the preset region corresponds to a region in which the central point position of the user's pupil is located when the user's eye stares at a center of the screen, and wherein the image comprises a plurality of pixels; and after recognizing that the user has stared at the first object for the preset time, a process of performing a second task causing at least one object, which induces the user's gaze to move to a region other than the first region instead of the first object on the screen of the user terminal, configured to be displayed in a region other than the first region, wherein the first task and the second task are performed a preset number of times;

a process of causing the at least one camera of the user terminal to acquire another image of the user's eye while the second task is performed the preset number of times;

by analyzing the another image of the user's eye, a process of generating gaze information related to the user while the second task is performed the preset number of times; wherein the gaze information comprises at least one of information on a number of times that the user correctly performed a preset gaze task, information on a number of times the user failed to perform the preset gaze task correctly, information on whether the user's gaze continues to stare at a specific point for the preset time, information on a time elapsed from a time point that a screen comprising the at least one object is displayed to a time point that the user's gaze moves to any one of the at least one object, information on a movement speed of the user's gaze, and information on whether the user's gaze is accurately staring at a point related to the preset gaze task;

a process of calculating a score by inputting the gaze information into a dementia identification model; and a process of determining whether the user has dementia based on the score;

wherein either:
(a) the at least one object comprises text: displayed instead of the first object on the first region; and a second object and third object respectively displayed in a second region and third region different from the first region; and the first region is located between the second region and the third region; and the preset gaze task comprises at least one of: a task to stare at an object related to a meaning of the text among the second object and the third object; and a task to stare at an object related to a color of the text among the second object and the third object; or (b) the at least one object comprises a gaze-inducing object displayed in any one area of a second region and third region different from the first region; and the first region is located between the second region and the third region; and the preset gaze task comprises a task to stare in a direction opposite to a direction in which the gaze-inducing object is located.

9. A device for identifying dementia of a user, the device comprising:

a storage configured to store at least one program instruction; and at least one processor configured to execute the at least one program instruction, wherein the at least one processor:

performs a first task causing a first object configured to be displayed on a first region of a screen displayed on a user terminal configured to induce the user's gaze of the user terminal to stare at the first region, causes at least one camera of the user terminal to acquire an image of the user's eye while the first task is performed;

recognizes, by analyzing the image of the user's eye acquired while the first task is performed, that the user is staring at the first object for a preset time by recognizing that a central point position of the user's pupil exists within a preset region, wherein the preset region corresponds to a region in which the central point position of the user's pupil is located when the user's eye stares at a center of the screen, and wherein the image comprise a plurality of pixels, and after recognizing that the user has stared at the first object for the preset time, performs a second task causing at least one object, which induces the user's gaze to move to a region of the screen other than the first region, instead of the first object on the screen of the user terminal, configured to be displayed in the region of the screen other than the first region, wherein the first task and the second task are performed a preset number of times;

causes the at least one camera of the user terminal to acquire another image of the user's eye while the second task is performed the preset number of times;

by analyzing the another image of the user's eye, generates gaze information related to the user while the second task is performed the preset number of times; wherein the gaze information comprises at least one of information on a number of times that the user correctly performed a preset gaze task, information on a number of times the user failed to perform the preset gaze task correctly, information on whether the user's gaze continues to stare at a specific point for the preset time, information on a time elapsed from a time point that a screen comprising the at least one object is displayed to a time point that the user's gaze moves to any one of the at least one object, information on a movement speed of the user's gaze, and information on whether the user's gaze is accurately staring at a point related to the preset gaze task;

calculates a score by inputting the gaze information into a dementia identification model; and determines whether the user has dementia based on the score;

wherein either:
(a) the at least one object comprises: text displayed instead of the first object on the first region; and a second object and third object respectively displayed in a second region and third region different from the first region; and the first region is located between the second region and the third region, and the preset gaze task comprises at least one of: a task to stare at an object related to a meaning of the text among the second object and the third object; and a task to stare at an object related to a color of the text among the second object and the third object; or (b) the at least one object comprises a gaze-inducing object displayed in any one area of a second region and third region different from the first region; and the first region is located between the second region and the third region; and the preset gaze task comprises a task to stare in a direction opposite to a direction in which the gaze-inducing object is located.

10. The method of claim 1, wherein:
analyzing the image of the user's eye comprises comparing a color value of a pixel of the image of the user's eye to a preset threshold value to determine a position of the user's pupil.

11. The method of claim 1, wherein:
the method comprises performing a binarization process of changing a first part of the image of the user's eye corresponding to a position of the user's pupil to a first color, and changing a second part of the image of the user's eye corresponding to a second color; and analyzing the image of the user's eye comprises, after the binarization process, distinguishing the first part of the image of the user's eye from the second part of the image.

12. The computer program of claim 8, wherein:
analyzing the image of the user's eye comprises comparing a color value of a pixel of the image of the user's eye to a preset threshold value to determine a position of the user's pupil.

13. The computer program of claim 8, wherein:
the processes comprise a binarization process of changing a first part of the image of the user's eye corresponding to a position of the user's pupil to a first color, and changing a second part of the image of the user's eye corresponding to a second color; and
analyzing the image of the user's eye comprises, after the binarization process, distinguishing the first part of the image of the user's eye from the second part of the image of the user's eye.

14. The device of claim 9, wherein:
analyzing the image of the user's eye comprises comparing a color value of a pixel of the image of the user's eye to a preset threshold value to determine a position of the user's pupil.

15. The device of claim 9, wherein:
wherein the at least one processor performs a binarization process of changing a first part of the image of the user's eye corresponding to a position of the user's pupil to a first color, and changing a second part of the image of the user's eye corresponding to a second color; and
analyzing the image of the user's eye comprises, after the binarization process, distinguishing the first part of the image of the user's eye from the second part of the image of the user's eye.

* * * * *